(12) United States Patent
Beltmann et al.

(10) Patent No.: US 8,416,084 B2
(45) Date of Patent: Apr. 9, 2013

(54) WIRELESS PATIENT MONITORING SYSTEM

(75) Inventors: Marc Beltmann, Oconomowoc, WI (US); Brad Johansen, Milwaukee, WI (US)

(73) Assignee: Direct Supply, Inc., Milwaukee, WI (US)

( * ) Notice: Subject to any disclaimer, the term of this patent is extended or adjusted under 35 U.S.C. 154(b) by 700 days.

(21) Appl. No.: 12/631,237

(22) Filed: Dec. 4, 2009

(65) Prior Publication Data

US 2011/0133935 A1    Jun. 9, 2011

(51) Int. Cl.
*G08B 23/00* (2006.01)

(52) U.S. Cl.
USPC .......... 340/573.1; 340/539.12; 340/539.1

(58) Field of Classification Search .................. None
See application file for complete search history.

(56) References Cited

U.S. PATENT DOCUMENTS

| | | | |
|---|---|---|---|
| 2001/0034475 A1* | 10/2001 | Flach et al. | 600/300 |
| 2007/0229249 A1* | 10/2007 | McNeal et al. | 340/524 |
| 2008/0204201 A1* | 8/2008 | Perkins et al. | 340/286.07 |
| 2008/0272918 A1* | 11/2008 | Ingersoll | 340/573.1 |

* cited by examiner

*Primary Examiner* — Travis Hunnings
(74) *Attorney, Agent, or Firm* — Boyle Fredrickson, S.C.

(57) ABSTRACT

A wireless patient monitoring system employs room units to collect and display information from a variety of room based sensors, the latter of which may be battery-powered and have low range. The room units may relay collected data from the associated sensor units and, as identified to the room unit, to a central controller.

19 Claims, 8 Drawing Sheets

WIRELESS PATIENT MONITORING SYSTEM

BACKGROUND OF THE INVENTION

Hospital and residential care facilities may provide nurse call systems allowing patients, residents, and/or caregivers (henceforth the system and method will reference actions made by the patient, although one of ordinary skill in the art should recognize that the actions and/or description may apply to any person) to request assistance at times between regularly scheduled rounds. For patients, who may need additional assistance in caring for themselves, the nurse call systems may be augmented with sensing systems that, for instance, indicate that a patient has moved from a chair or bed and thus may need assistance or monitoring. Such systems may, for example, use pressure pads placed in a bed or a chair to indicate that the occupant has risen or similar pads used as floor mats near a bed to detect that the occupant has stepped down onto the floor. Such pads incorporate switches to provide an electrical signal when activated. Tether systems that clip to a patient's clothing, may also be used for monitoring a patient's movement.

These patient-sensing systems may provide an indication, such as a visual indication, a simple buzzer or audio alarm, etc. to signal the caregiver. Such audible systems have limited range and accordingly it is also known to incorporate a radio transmitter into the sensor to provide a signal at a central monitoring unit. The central monitoring unit may provide, for example, a display that may distinguish among multiple different sensor units. For sensor units that are much removed from the central monitoring unit or blocked by radio absorbing materials, radio relays may be used to boost the signal on route to the central monitoring unit.

Wireless central monitoring provides the benefit of allowing a single individual to monitor multiple patients; however, a gap in care can occur when the monitoring caregiver must go attend to a particular patient and leave the central monitoring unit unattended. Locating the particular sensor being activated can be difficult depending on the detail provided by the central monitoring station. In addition, programming the central monitoring unit can be cumbersome, particularly when sensors are changed for a particular patient, for example between the use of a chair pad and bed pad. Current battery powered wireless sensors, while simple to install, require a regular program of inspecting the sensors and recharging their batteries, if indicated, to prevent loss of monitoring capability.

SUMMARY OF THE INVENTION

The present invention provides a wireless sensing system that greatly simplifies programming the central monitoring unit by logically collecting signals from sensors in a given room at an associated room unit. The room unit may then forward the signals to the central monitoring unit which may display room location and alarm type without previous registration of each sensor with the central monitoring unit. Significantly, once the room units are associated with the central unit, sensor units may be freely exchanged at the room level without reprogramming the central monitoring unit.

A room unit, associated with each room, may also provide a visual display of the location of the alarm for the responding caregiver now removed from the information of the central monitoring station. The room unit may be powered by line power and, by locally boosting the signal from the sensors, may significantly decrease the battery drain of the sensors prolonging battery life almost indefinitely.

Specifically then, the present invention may provide a wireless monitoring system having multiple sensor units each having an input triggerable by a patient (either intentionally or by patient action) and transmitting a first radio signal including sensor identification data, uniquely identifying the sensor unit, and state data indicating a triggering of the input. At least one room unit may receive the first radio signals of the sensor units and include a connection table mapping identification data to the room unit. The room unit selectively responds to first radio signals of sensor units mapped to the room unit by the connection table to transmit a second radio signal including state data from the first radio signals as well as room unit identification data uniquely identifying the room unit.

At least one central unit may receive the second radio signals, the central unit including a room table mapping room unit identification data to room identifiers (for example, a room number or a patient's name) to provide at least one of an audio alarm and a visual display indicating the triggering of sensor units linked and the room identifier. While the room units can stand alone, it is thus one feature of at least one embodiment of the invention to provide, through dedicated room units, an improved networking of sensors to a central monitoring unit.

It is thus one feature of at least one embodiment of the invention to provide, through dedicated room units, an improved networking of sensors to a central monitoring unit.

The first radio signal may further include function data identifying a function of the sensor unit and thus the meaning of the triggering of the sensor unit. The function data may indicate, for example, a state of a bed pressure pad, a state of a chair pressure pad, a state of a floor pressure pad, or a state of a patient call button.

It is thus one feature of at least one embodiment of the invention to distinguish among multiple sensors simultaneously used in a room. It is another feature of at least one embodiment of the invention to permit different sensor functionalities to be seamlessly integrated in a single system. It is another feature of at least one embodiment of the invention to provide for a high degree of flexibility in selecting and changing sensors for a particular patient without the need for additional network programming.

The display provided at the central monitoring unit may be, but is not limited to, at least one of a room number, a patient name, symbols, alarm triggering time, the name of a caregiver resetting the alarm, and graphic data indicating a room location.

It is thus one feature of at least one embodiment of the invention to permit the display of detailed room-based information in the central unit alarm, such as may be manually entered and linked to a room unit, while minimizing the data entry necessary to enroll each sensor.

The room unit may provide at least one of an audio and/or visual alarm and a display indicating a triggering of an input of sensor units mapped to the room unit.

It is thus one feature of at least one embodiment of the invention to provide guidance to a monitoring caregiver en route to a patient room as to the location of the triggered sensor and to notify the caregiver of new alarm conditions when the caregiver is removed from the central control unit.

The room unit display may indicate function data of sensor units whose state data indicates a triggering of an input of the sensor units.

It is thus one feature of at least one embodiment of the invention to allow a caregiver to readily distinguish among alarm conditions during an approach to the room.

The display may indicate a triggering of an input of a sensor unit through a selected light color and light-flashing pattern.

It is thus one feature of at least one embodiment of the invention to provide a visual indication that may be easily read by both those with normal vision and with certain forms of color-blindness.

The sensor units may use a battery power supply and the room unit a line voltage power supply.

It is thus one feature of at least one embodiment of the invention to substantially reduce the power drain on the battery powered sensor units by greatly limiting their necessary transmission range.

The first radio signal may further include battery data indicating battery strength.

It is thus one feature of at least one embodiment of the invention to provide a system that eliminates the need for inspection at each of spatially separated sensor units on a regular basis by collecting such information at the central monitoring unit.

The room unit may include a reset button causing the transmission of the second radio signal to the central monitoring unit indicating a caregiver response to the triggering of a sensor unit.

It is thus one feature of at least one embodiment of the invention to permit simple and visible deactivation of an alarm using a switch on a stationary device that may be readily located. It is another feature of this embodiment of the invention to simplify the sensor units by moving an alarm resetting feature to the room unit. It is another feature of this embodiment to prevent tampering by moving the alarm resetting feature away from the sensor to the room unit.

The room unit may include a feature that populates a connection table based on the received signal strength of identification data from the sensor in the first radio signal at a time when the sensor unit is in close proximity of the room unit. It is another feature of this embodiment of the invention to provide the user one type of visual and auditory feedback when the connection table is successfully populated, and another type of visual and auditory feedback when it is not successfully populated.

It is thus one feature of at least one embodiment of the invention to provide a simple and intuitive networking system that makes network connection simply by bringing units together, avoiding the need for complex network initialization protocols. It is another feature of this embodiment of the invention to provide a network connection system that permits ready interchange of sensors without transporting them to the central monitoring unit.

The room unit connection table may be depopulated when the sensor unit is within close proximity of the room unit, and the room unit receives identification data from the sensor that exceeds a pre-determined signal strength, and the sensor unit is already enrolled in the connection table. It is another feature of this embodiment of the invention to provide the user one type of visual and auditory feedback when this connection table is successfully depopulated, and another type of visual and auditory feedback when the connection table is not successfully depopulated.

It is thus one feature of at least one embodiment of the invention to permit simple reconfiguration of the network, for example, by removing sensors.

The central unit may include a feature that populates a connection table based on the received signal strength of identification data from the room unit at a time when the room unit is in close proximity of the central unit. It is another feature of this embodiment of the invention to provide the user one type of visual and auditory feedback when the connection table is successfully populated, and another type of visual and auditory feedback when it is not successfully populated.

The central unit connection table may be depopulated when the room unit is within close proximity of the central unit, and the central unit receives identification data from the room unit that exceeds a pre-determined signal strength, and the room unit is already enrolled in the connection table. It is another feature of this embodiment of the invention to provide the user one type of visual and auditory feedback when this connection table is successfully depopulated, and another type of visual and auditory feedback when the connection table is not successfully depopulated.

It is thus one feature of at least one embodiment of the invention to provide for a consistent network formation system that may be used for each component of the invention in an intuitive manner.

These particular features and advantages may apply to only some embodiments falling within the claims and thus do not define the scope of the invention.

BRIEF DESCRIPTION OF THE FIGURES

FIG. 6 is a figure similar to that of FIG. 2 showing positioning of the room unit proximate to the central monitoring unit to establish a network relationship there between;

DETAILED DESCRIPTION OF THE PREFERRED EMBODIMENT

Components of the Wireless Monitor System

Figure 1:
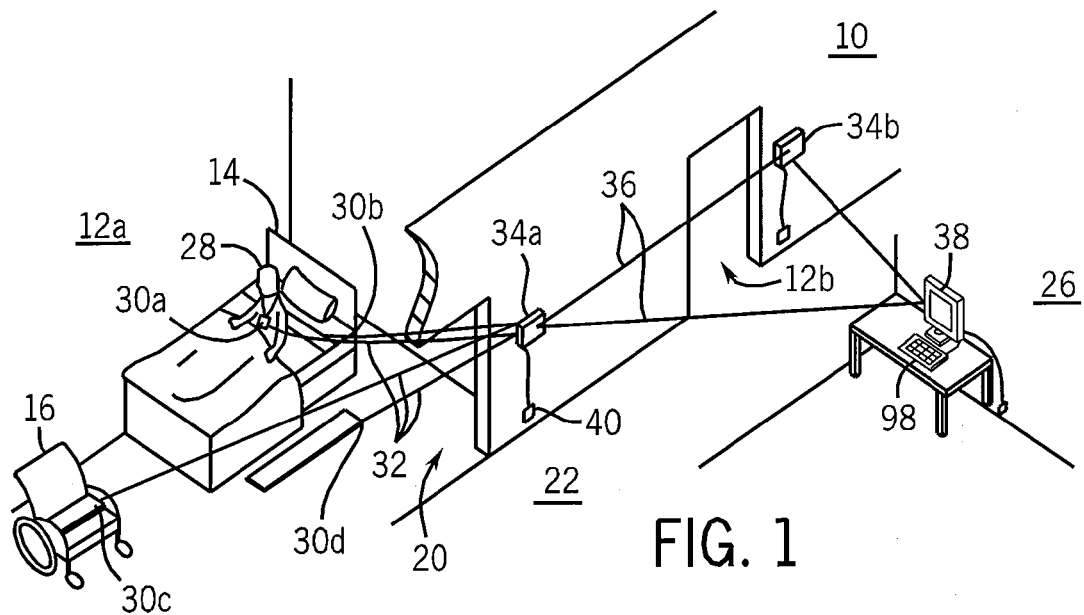
FIG. 1 is a perspective view in partial cut away of a long term care facility employing the wireless patient monitoring system of the present invention having in-room sensor units, wall-mounted room units dedicated to a particular room and a central monitoring unit reading data aggregated by the room units.

Referring now to FIG. 1, a long term care or other facility 10 suitable for use with the present invention may provide for a patient room 12a, for example, holding a patient bed 14, a chair 16, and communicating through a door 20 with a hallway 22 leading past other rooms 12b and a central monitoring area 26.

A patient 28 in the room 12a may be monitored with a set of different sensor units 30a-30d used alone or alternatively. In this example, sensor unit 30a is a patient call button on a lanyard about the patient 28. Sensor unit 30b may be associated with a bed pressure pad indicating whether the patient 28 is lying in the bed 14 or has risen. Sensor unit 30d may be associated, for example, with a floor pad positioned to activate when the patient 28 steps down out of the bed 14. The sensor unit 30c may be associated with a chair pad providing a similar function as the bed pad associated with sensor unit 30b but for a chair.

Although pressure sensors are shown and described with reference to FIG. 1, it should be understood that the sensor may be associated with a variety of types of alarms, such as mobile/common area alarms, equipment monitoring alarms, elopement alarms, resident activities of daily living (ADL) monitoring, etc. Further, although the sensors are described as pressure sensors, other sensor types may include chemical sensors, thermal sensors, power sensors, equipment sensors, etc.

The sensor units 30a-30d may communicate by radio signals 32 with a room unit 34, for example, mounted outside of the door 20. Generally the distance between any given sensor unit 30 and the room unit 34 will be relatively short and on the order of the dimensions of the room 12a. The room unit 34 may, in turn, communicate wirelessly as indicated by radio signals 36 with either the central monitoring unit 38 or another room unit 34 acting as a relay between the room unit 34a and central monitoring unit 38. Normally, as will be described below, each of the sensor units 30 will be battery-powered and thus it is desired to conserve power used transmitting radio signals 32. In contrast, room units 34 normally will be powered through power line connections 40 (shown as a wall transformer) to have access to substantially unlimited electrical energy. The room units 34 may thus use higher powered transmissions. This, and the ability to use other room units 34 as a relay, permits the distance between a given room unit 34 and the central monitoring unit 38 to be arbitrarily large. Room units 34 may also include a battery power option in the event of a power failure.

Although the room units 34 are described as being one system in communication with the central monitoring unit 38, room units 34 may operate as independent sensor data aggregators and sensor feedback displays. Further, each room unit 34 may be configured to communicate with a pass signals from other room units 34 to extend transmission range, provide a network of room units, etc. According to an alternative embodiment, room units 34 may be also configured to communicate alarm conditions from any sensor unit 30 within range, such that an alarm condition may still be communicated in the event of failure of any one room unit 34.

Figure 2:
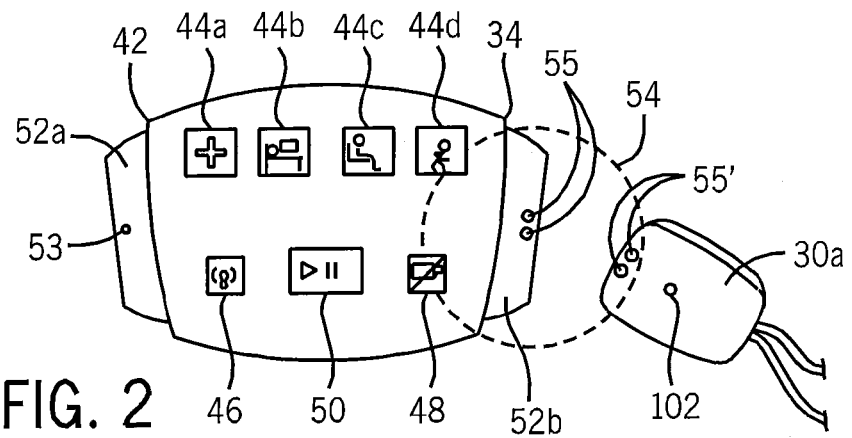
FIG. 2 is a front elevational view of the room unit of FIG. 1 showing its indicator lights and reset button and showing the positioning of a sensor unit proximate to the room unit to establish a network relationship.

Referring now to FIG. 2, each room unit 34 may have a front panel 42 displaying sensor state indicators 44 which may be illuminated by internal lamps (LEDs) to be green, yellow or red, the meaning of which will be described below. Each of these indicators 44a-d may be associated with a particular type of sensor unit 30 (that is, having a different function) and may be marked with a distinctive icon representing the function of the associated sensor independent of an understanding of a particular language. Thus, for example, sensor indicator 44 exhibits a cross indicating a nurse call sensor unit 30a, sensor indicator 44b exhibits a stylized bed indicating a bed pad sensor unit 30b, sensor indicator 44c exhibits a stylized chair denoting a chair pad sensor unit 30c, a and sensor indicator 44d provide a stylized walking individual indicating a floor pad sensor unit 30d.

The front panel 42 may also include a lost signal indicator 46 and a low battery indicator 48 that may be illuminated with a solid (non-flashing) red lamp when activated as will be described below. The lost signal indicator 46 indicates a loss of radio connection with a sensor whereas the low battery indicator 48 indicates a sensor having a low battery that needs replacement or recharging. The low battery indicator for the room alarm may also be displayed on the front panel 42. Centered between lost signal indicator 46 and low battery indicator 48 is a reset button 50 that may be pressed by a caregiver to reset an alarm condition. So that the caregiver may reach the reset button 50, the room unit 34 is preferably mounted at a distance above the floor that may be reached by individuals at a range of different heights.

Figure 11:
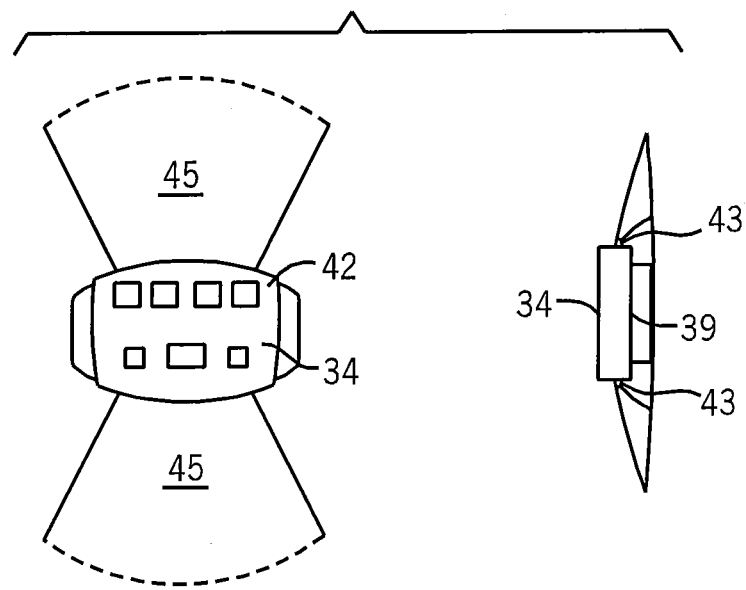
FIG. 11 is a front and side view of the room unit mounted on a wall showing the use of light bars to create a large area display.

Referring momentarily to FIG. 11, the mounting of the room unit 34 preferably uses a releasable bracket 39 or keyhole slots in a housing of the room unit 34 that releasably engage wall screws to allow the room unit 34 to be removed from the wall and taken to the central monitoring area 26 to make a network connection with the central monitoring unit 38 as will be described. As shown in FIG. 11, light bars 43 (light emitting diode strips) may be mounted along upper and lower edges of the front panel 42 to cast sector shaped projections 45 on the wall behind the room unit 34 substantially increasing its visibility during an alarm condition.

Logical Connection of the Components

Left and right portions 52a and 52b of the housing of the room unit 34 flanking the front panel 42 may be marked with a single dot 53 on left portion 52a and a double dot 55 on right portion 52b. This single dot 53 and double dot 55 indicate targets for network connection creation and deletion, such as defines the logical interconnections between the sensor units 30, the room units 34 and the central monitoring unit 38.

"Logical interconnection" in this context refers to the intended endpoints of communication and thus is to be distinguished from the actual route of the data which may pass from room unit 34a to room unit 34b, for example, even though data from room unit 34a is not intended for room unit 34b but only for central monitoring unit 38. The process of logically connecting a sensor unit 30 with a room unit 34 will practically result in the room unit 34 being responsive only to the alarm signals of sensor units 30 that are logically connected to it. Likewise the central monitoring unit 38 will only be responsive to room units 34 that are logically connected to it.

To make a logical connection between a room unit 34 and sensor unit 30a, for example, sensor unit 30a is brought within a close-proximity radius 54 of the right portion 52b. The sensor unit 30a has two dots 55' marked on one end of it indicating the correct orientation of the sensor unit 30a and the side of the room unit 34 that must be approached.

Figure 3:
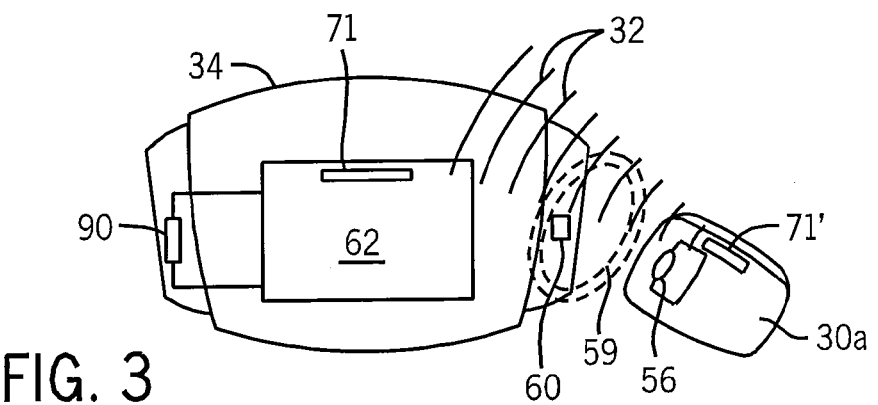
FIG. 3 is a figure similar to that of FIG. 2 with the room unit in phantom showing elements of a proximity sensing system employing a magnetic field in conjunction with the received radio signal to provide for a networking connection.
Figure 4:
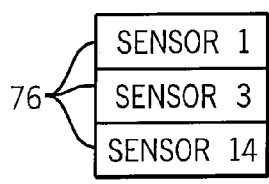
FIG. 4 is a representation of a connection table stored by the room unit to identify its associated sensors per the procedure described with respect to FIG. 3.

Referring now to FIG. 3, each sensor unit 30 may include a proximity sensor 56 positioned near the end of the sensor unit 30 marked with the two dots 55'. A magnetic field 59 produced by a permanent magnet 60 within the right portion 52b of the room alarm may activate the proximity sensor 56 (in this case a reed switch) within the end of the sensor unit 30 when it is within the close-proximity radius 54. This radius 54 is generally much smaller than the limit of radio communication between the sensor unit 30a and the room unit 34 and will typically be on the order of 2 inches or less.

Figure 5:
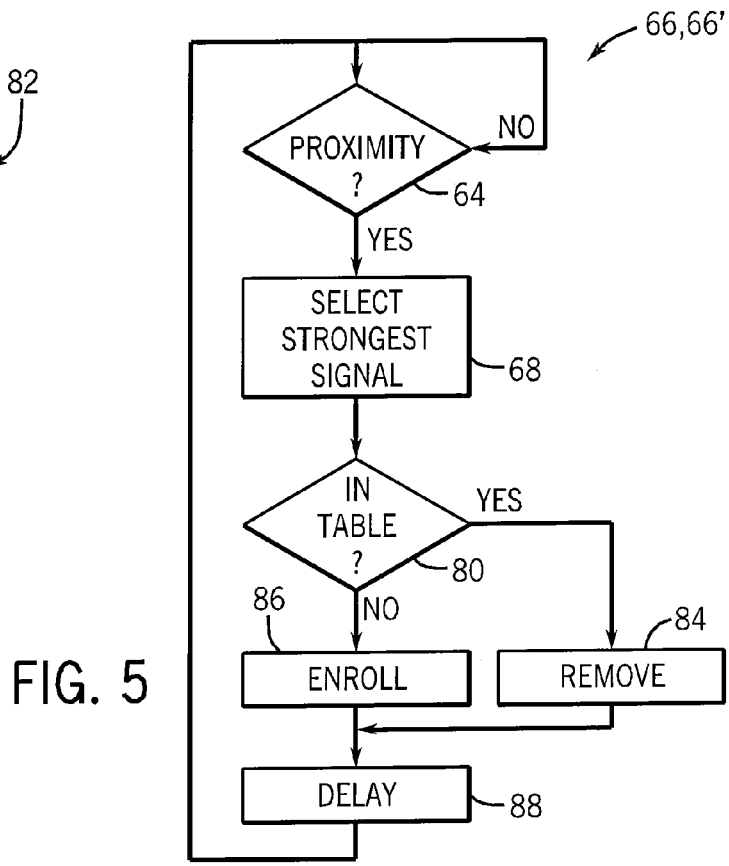
FIG. 5 is a flow chart of a program executed by either the room unit or central unit when generating network connections.

Referring now to FIG. 5, when proximity sensor 56 within the sensor unit 30a is activated, a pairing signal is transmitted, which is received by room unit 34. After reception, a control program 66, triggered by decision block 64, is executed by the control circuit 62 on the room alarm 32. At this time, as indicated by process block 68, the control circuit 62 identifies that the pairing signal 32 being received at antenna 71 is from the sensor unit 30, and that the signal exceed a predetermined signal strength.

Figure 8:
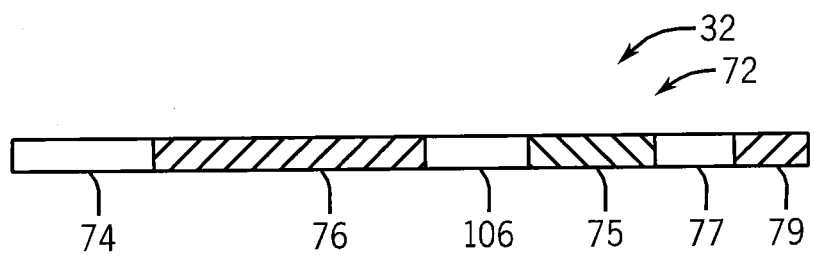
FIG. 8 is a logical representation of a radio signal sent from a sensor unit to the room unit.

Referring now momentarily to FIG. 8, data packet 72 transmitted from the sensor unit 30 will generally have a control header 74 related to the particular protocol of the network system followed by a sensor identification number 76 unique to the particular sensor unit 30, a sensor type 75, a sensor registration status field 77, a sensor contact state 106, and a sensor battery state 79.

Referring again to FIG. 5, after the pairing signal is confirmed to above the predetermined signal strength, at process block 68 the control circuit 62 captures the sensor identification number 76 from the received pairing signal.

At succeeding decision block 80, the program 66 investigates a connection table 82 listing the unique sensor identification number 76 of all logically connected sensor units 30. If the signal from the sensor unit 30 identified at that process block 68 is not in the connection table 82, then the program 62 proceeds to process block 86 and the sensor identification number 76 is written in the table 82. This act logically connects the sensor unit 30 and the room unit 34 so that the room unit 34 will be responsive to signals from the sensor unit 30 and will forward its data to the central monitoring unit 38.

According to an exemplary embodiment, room unit 34 may be configured to include one instance of several different types of sensors, such as a chair sensor, a bed sensor, a nurse call sensor, etc. Accordingly, room unit 34 may be configured to provide an alarm if more than one instance of a particular type of sensor is attempted to be registered to a single room unit 34. Similarly, sensors may be configured to detect if they are being registered to more than one room unit 34. According to an alternative embodiment, different types of room units may be configured to allow registrations for multiple instance of the same type of sensor (e.g., a room unit for a common area may accept several chair sensors).

On the other hand if the sensor identification number 76 associated with the signal detected at process block 68 is already enrolled in the connection table 82, then the sensor unit 30 is logically disconnected by having its sensor identification number 76 erased.

In either case, after the delay indicated by process block 88, for example five seconds, the program is repeated. During the delay of process block 88, the corresponding sensor indicator 44 on the room unit 34 flashes one color, and the room unit 34 emits one type of tone, to indicate the function of the connected sensor unit 30 being connected and to provide for confirmation to the user. If the sensor pairing/unpairing fails at any point of the process, the corresponding sensor indicator 44 on the room unit 34 flashes a different color, and the room unit 34 emits a second tone, to provide feedback to the user that the pairing/unpairing was not successful.

It will thus be understood that connection of a sensor unit 30 to a room unit 34 may be effected simply by bringing the two units together for a short period of time. The same process can be used to remove a pre-connected sensor unit 30. The five-second delay of process block 88 prevents rapid successive adding and removing of the sensor in a given session inadvertently.

The sensor units 30b-30d which are associated with pressure pads, may be removed from their pads by releasable electrical connectors for the purpose of making this network connection.

Figure 6:
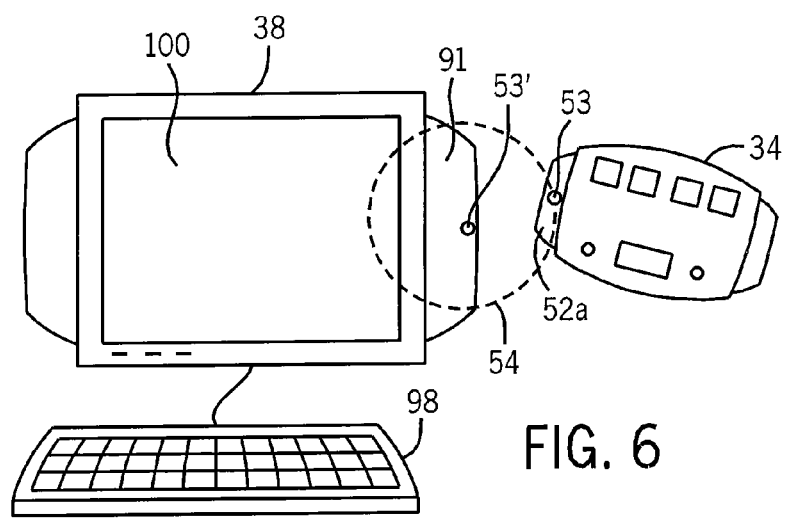

Referring again to FIG. 3, the left portion 52a of the room unit 34 provides a single dot 53 and incorporates a proximity sensor 90 similar to the proximity sensor 56 in sensor unit 30. Referring to FIG. 6, a similar procedure may then be used to connect the room unit 34 to particular central monitoring unit 38. In this case, the single dot 53 on the left portion 52a of the room unit 34 is brought within the close-proximity radius 54 of a single dot 53' on a right-hand portion 91 of the central monitoring unit 38 which may also hold a permanent magnet.

Figure 9:
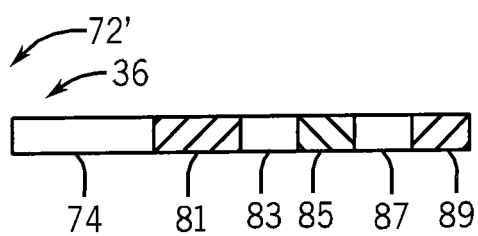
FIG. 9 is a logical representation of a radio signal sent from a room unit to the central monitoring unit.

Referring momentarily to FIGS. 5 and 9, the central monitoring unit 38 executes a program 66' substantially identical to that executed by the room unit 34 with the exception that the program executed by the central monitoring unit 38 detects radio signals 36 from the room unit 34 providing data packets 72'. Data packets 72' will generally have a control header 74 related to the particular protocol of the network system followed by a room unit identification number 81 unique to the particular sensor unit 30, a room unit type 83, a room unit registration status field 85, a room unit sensor status field 87, and a room unit battery state 89.

Figure 7:
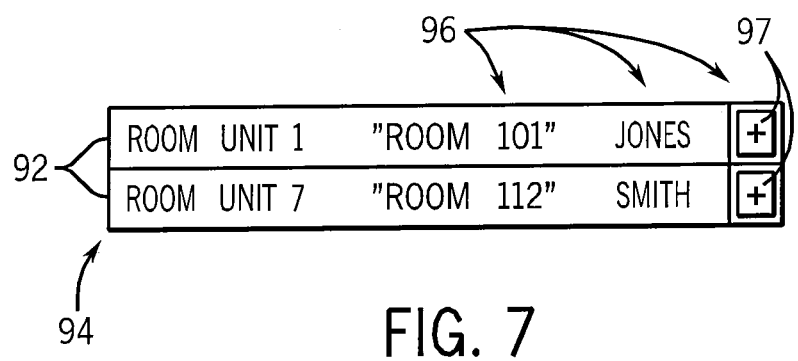
FIG. 7 is a figure similar to that of FIG. 4 showing a room table stored by the central monitoring unit and manually populated with room identifying information.

Referring now also to FIG. 7, the central monitoring unit 38 provides a room table 94 comparable to connection table 82 but linking the room unit identification number 92 to one or more room identifiers 96, for example a text string such as "room 101" or the name of the patient occupying the room, e.g. "Jones". The room identifiers 96 may be entered by means of a keyboard 98 attached to the central monitoring unit 38 at the time of the logical connection of the central monitoring unit 38 to a room unit 34. This data entry may be prompted by on-screen instructions during process block 86 of FIG. 5. The room identifier 96 may alternatively be a graphic representation 97 of the room as will be described below with respect to FIG. 13.

Note that the logical connections between a room unit 34 and sensor units 30 may be done in any order with respect to connections with other sensor units 30 and/or between room unit 34 and the central monitoring unit Operation of the Monitoring System Referring now again to FIG. 1, in use, a given sensor unit 30 may be triggered by the patient 28, for example by pressing a button 102 (shown in FIG. 2) on a pendant associated with sensor unit 30a, removal of pressure from pads associated with sensor units 30b or 30c or the introduction of pressure on the floor pad associated with sensor unit 30d.

Immediately upon any of these occurrences (that is, possibly before the expiration of the ninety second periodic pulse schedule) a data packet 72 of radio signal 32 shown in FIG. 8 may be transmitted by the corresponding sensor unit 30. As noted above, each of these data packets includes a sensor identification number 76. The data packet 72 may also include a sensor type field 75 indicating the type of sensor sending the signal. The data packet 72 may also include a sensor registration status field 77, indicating whether the sensor has been previously paired with a room unit. The data packet may also include a state change field 106 indicating a change of state of the sensor unit 30 either from triggered to un-triggered or un-triggered to triggered of the sensor unit 30. Alternatively the actual state of the sensor unit (triggered or un-triggered) may be transmitted upon the occurrence of the state change. The data packet 72 also includes a battery health field 108 providing indication of the strength of the battery. These signals will be continued to be transmitted every ninety seconds even absent another state change.

Referring again to FIG. 1, upon receipt of the data packet 72 by a room unit 34a having the sensor identification number 76 of the data packet 72 in its connection table 82, a second radio signal 36 is broadcast by the room unit 34a. As indicated in FIG. 9, the second radio signal 36 includes a data packet 72', which includes a room unit identification number 81. The data packet 72' may also include a room unit type field 83 indicating the type of room unit sending the signal. The data packet 72' may also include a room unit registration status field 85, indicating whether the room unit has been previously paired with the central monitoring unit. The data packet may also include a sensor status field 87 indicating the current status of all of the sensors currently registered to the room unit. The data packet 72' also includes a battery health field 89 providing indication of the strength of the room unit battery. These signals will be continued to be transmitted every ninety seconds even absent another state change.

This data packet may proceed directly to the central monitoring unit 38 or may pass through one or more other room units 34 acting as relays.

The central monitoring unit 38 will respond only to those packets 72' containing room unit identification number 92 enrolled in its room table 94 shown in FIG. 7.

Central monitoring unit 38 may be configured to perform any number of functions based on the received packets. Exemplary actions include relaying the information in the packet to a pager, providing visual and/or audio indications, logging the received data, etc.

According to an exemplary embodiment, central monitoring unit 38 and/or room units 34 may be configured to transmit information to a pager network (not shown). The pager network may be configured to utilize a communication network established by a plurality of network devices to send and receive information. Information sent through the network may be continuously retransmitted by the network devices until received by a pager device. The pager device may be configured to transmit an acknowledgement message to confirm receipt of the information. Advantageously, communicating information to pagers using the network of room units described herein allows pages to be transmitted even in the event of failure of one or more room units. Although a particular pager network configuration is described herein, it should be understood that system 10 may also be configured to utilize a standard paging system.

Figure 12:
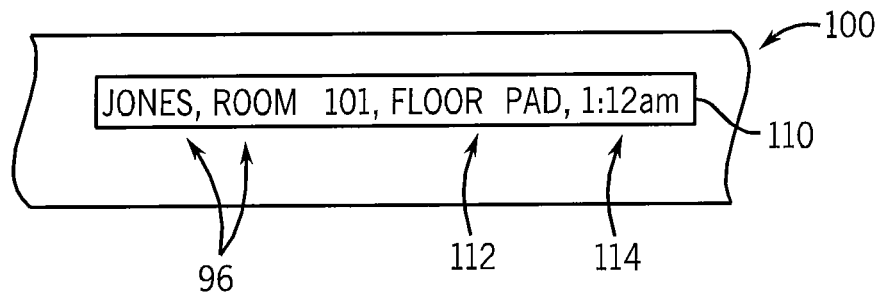
FIG. 12 is a fragmentary view of a display produced by the central monitoring unit in an alarm condition.
Figure 13:
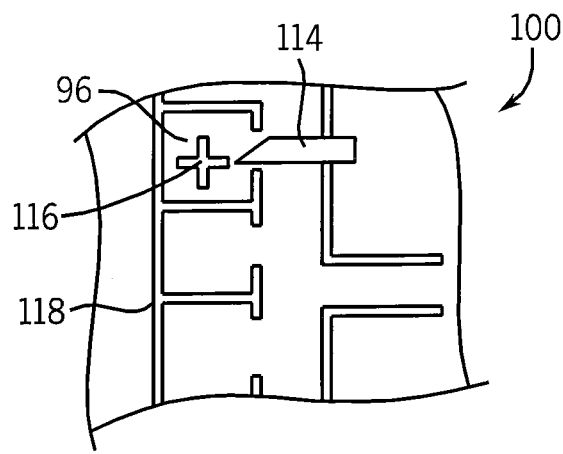
FIG. 13 is a fragmentary view of a display of an alternative graphic display produced by the central monitoring unit.

Referring now to FIG. 12, upon receipt at the central monitoring unit 38 of a data packet 72' from a logically connected room unit 34, if the sensor status field 87 indicates an alarm condition, the display screen 100 of the central monitoring unit 38 may provide a readout 110 indicating the room identifiers 96, a function identifier 112 derived from the function information contained in the sensor identification number 76, and a time 114 that an alarm was received as obtained from a local clock in the central monitoring unit 38. Alternatively, as shown in FIG. 13, a graphic room identifier 96 may be adopted, one example of which might be a blinking function symbol 116 on a map or other representation 118 of the facility 10, where the function symbol 116 provides for information comparable to the function identifier 112 and the location of the function identifier 112 identifies the room. The function symbol 116 may be accompanied with a caption showing the time 114.

Either text or graphic display may be accompanied by an audible alarm such as a beeping tone or voice message.

Referring now to FIG. 2, contemporaneously with the presentation of alarm information at the central monitoring unit 38, an alarm is provided at the room unit 34a logically linked to the particular triggered sensor unit 30. This alarm may include a tone and the illumination of one or more of the indicators 44a-d by a blinking red light.

In an example response, a caregiver at the central monitoring area 26 may leave the central monitoring area 26 to travel to the room 12 of the triggered sensor unit 30. This room 12 will be readily identified by the corresponding room unit exhibiting the sector shaped projections 45 (shown in FIG. 11) and a flashing red sensor indicator 44 (depending on the particular sensor unit 30) as well as a possible tone. As the caregiver passes the room unit 34a, he or she may press the reset button 50 on the room unit 34 shown in FIG. 2. Generally this reset button 50 stops the alarm signal at the room unit 34 and the central monitoring unit 38 allowing the caregiver to correct the alarm condition.

Figure 10:
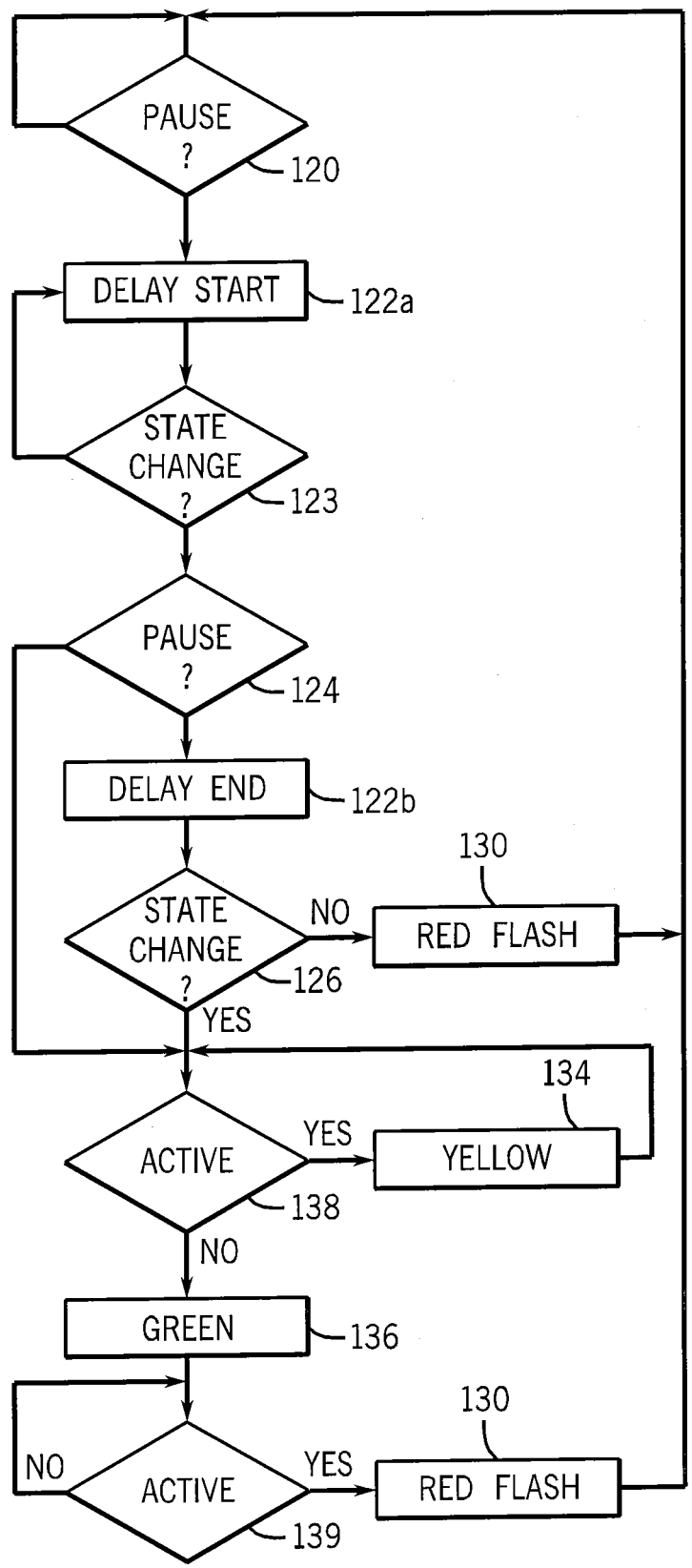
FIG. 10 is a flowchart executed by the room unit for controlling the room unit display.

Referring now to FIG. 10, referring to an embodiment of the room unit 34 having a pause button (not shown), specifically, a pressing of the reset button 58 may be detected by decision block 120 of program 66. The program then proceeds to delay block 122a which starts a delay timer, turns off the audible and/or flashing sensor indicator 44 on the room unit 34, and sends an appropriate radio signal 36 to the central monitoring unit 38 to suppress its alarm condition. Typically the delay timer will allow sufficient time for the alarm condition to be addressed but not so long that a significant gap in monitoring is created. The delay timer may be set, for example, to 60 seconds. If the sensor unit 30 causing the triggering changes state during the delay period as indicated by decision block 123 then the delay time is reset.

At any time during the delay period, a pause button may be pressed again which will cause the program to proceed to decision block 138 to assess the current sensor unit state as will be described below.

At the conclusion of the delay period, indicated by process block 122b, the program proceeds to decision block 126 to determine if there has been any change in state of the sensor unit 30 (its associated pad or button) during the delay time bounded by process blocks 122a and 122b. If there has been no state change (implicitly meaning the alarm condition is still active), the program proceeds to process block 130 and the audible and/or flashing sensor indicators 44 on the room unit 34 are reactivated and an appropriate radio signal 36 is sent to the central monitoring unit 38 to reactivate its alarm condition. The program then loops back to decision block 120.

If there has been a change of state during the delay period, then the program proceeds to decision block 138 to determine whether the state of the sensor unit 30 is still an active alarming condition. If so, the program proceeds to process block 134 and the audible alarm is turned off, the flashing sensor indicator 44 on the room unit 34 becomes a steady yellow signal, and an appropriate radio signal 36 is sent to the central monitoring unit 38 to suppress its alarm condition. This situation may arise, for example, if at decision block 138 there is no pressure on a bed pad such as normally would indicate an alarm condition but in this case may indicate that the patient 28 has not yet been resettled. The program loops at decision block 138 until the alarm state ends at which time the program proceeds to process block 136 and the yellow indicator is set to a green state.

The program then proceeds to decision block 139 to monitor the sensor unit 30. When a trigger condition is again sensed the program proceeds to process block 130 as described above.

At any time during this process a low battery signal or a loss of wireless connectivity may be detected by the program 66 running in the room unit 34. The low battery signal may, for example, be detected by monitoring a voltage of the battery during a load condition, for example the transmission of the regular radio signal 32. The loss of wireless connectivity may be detected, for example, by a missing regular transmission of a data packet 72 from an enrolled sensor unit 30. These conditions cause a steady red illumination of the appropriate sensor indicator 44 associated with the sensor unit 30 together with an illumination of one lost signal indicator 46 or low battery indicator 48 as is appropriate until the condition is corrected. The steady red illumination of the sensor indicator 44 will be overridden by process blocks 134 and 130 described above.

The following Table I provides the meaning of the color and flashing pattern of the indicators 44

TABLE I

| Light State | Meaning |
| --- | --- |
| No light | Sensor is not logically connected with the room unit |
| Green | Sensor is logically connected with the room unit and is ready to detect a trigger |
| Yellow | Sensor is logically connected with the room unit but is not yet ready to detect a trigger because of sensor state |
| Pulsing red | Sensor is logically connected with the room unit and has been triggered by a sensor state |
| Solid red (no pulsing) | Sensor is logically connected with the room unit but the battery is low or the wireless signal has been lost |

Generally, the red light illuminating the indicators 44 will be substantially brighter than the green or yellow light to allow red-green colorblind caregivers to be able to differentiate between normal and alarming conditions. This goal is also provided by the flashing of the red light under certain alarm conditions. As noted, when there is a combination of conditions, for example, low battery or wireless signal lost and an alarm condition generated by a triggering of the sensor, the alarm condition takes precedent with respect to the above chart. Different ones of the indicators 44 may be in different conditions.

Component Architecture

Figure 14:
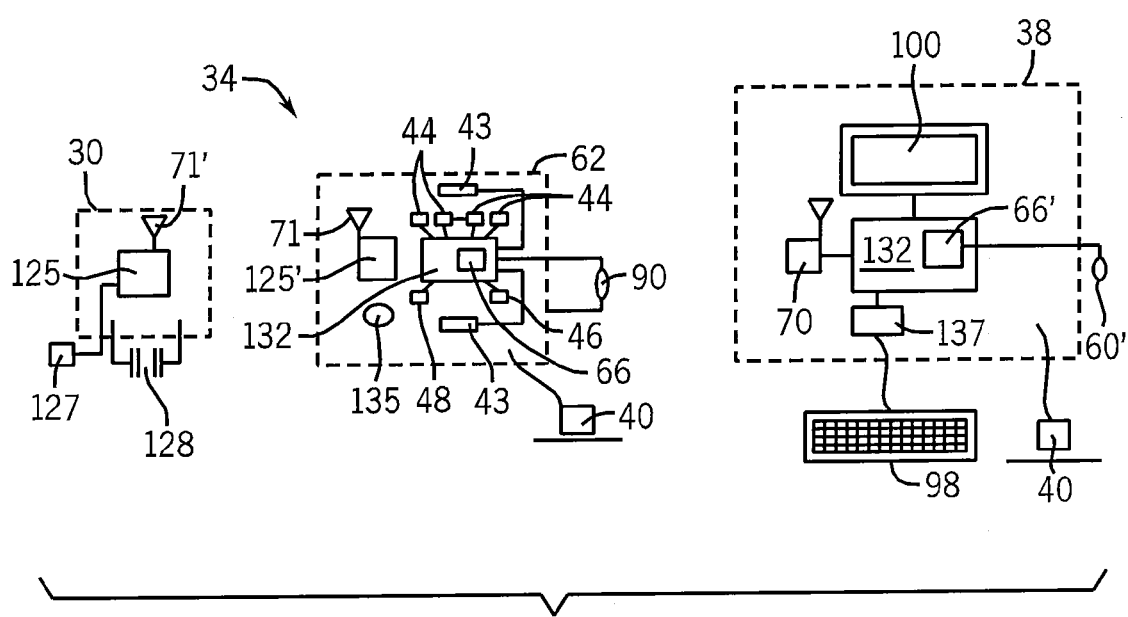
FIG. 14 is a set of simplified block diagrams of the hardware components of the sensor units, the room unit, and central monitoring unit of the present invention.

Referring now to FIG. 14, the sensor units 30 may be constructed using a single Zigbee module 125 based on the IEEE 802.15.4-203 standard and employing the associated microcontroller to execute any necessary programming to interface the Zigbee module 125 with an operator 127 such as a push button 102 or the pads described above with respect to FIG. 1.

The Zigbee module 125 is preferably powered solely by a battery 128 to eliminate interfering power wires and in the present application may provide extended operating times for each sensor unit 30 in excess of one year on a battery charge.

The room unit 34 may include a Zigbee module 125 communicating with a microcontroller 132 executing stored program 66, the microcontroller 132 providing signals to an audio alarm 135, the lost signal indicator 46, the low battery indicator 48, the light bars 43 and indicators 44, and receiving a signal from the proximity sensor 90. As noted above, the room unit 34 may be powered by power line connections 40, for example, through a wall transformer plugged into a standard electrical outlet.

The central monitoring unit 38 may also include a microcontroller 132 communicating with a Zigbee module 70 and providing a port 137, for example a USB port, communicating with a standard keyboard 98. The microcontroller 132 may execute stored program 66' as described to provide signals to a display screen 100. As with the room unit 34, the central monitoring unit 38 may be powered by a power line connection 40.

Figure 15A:
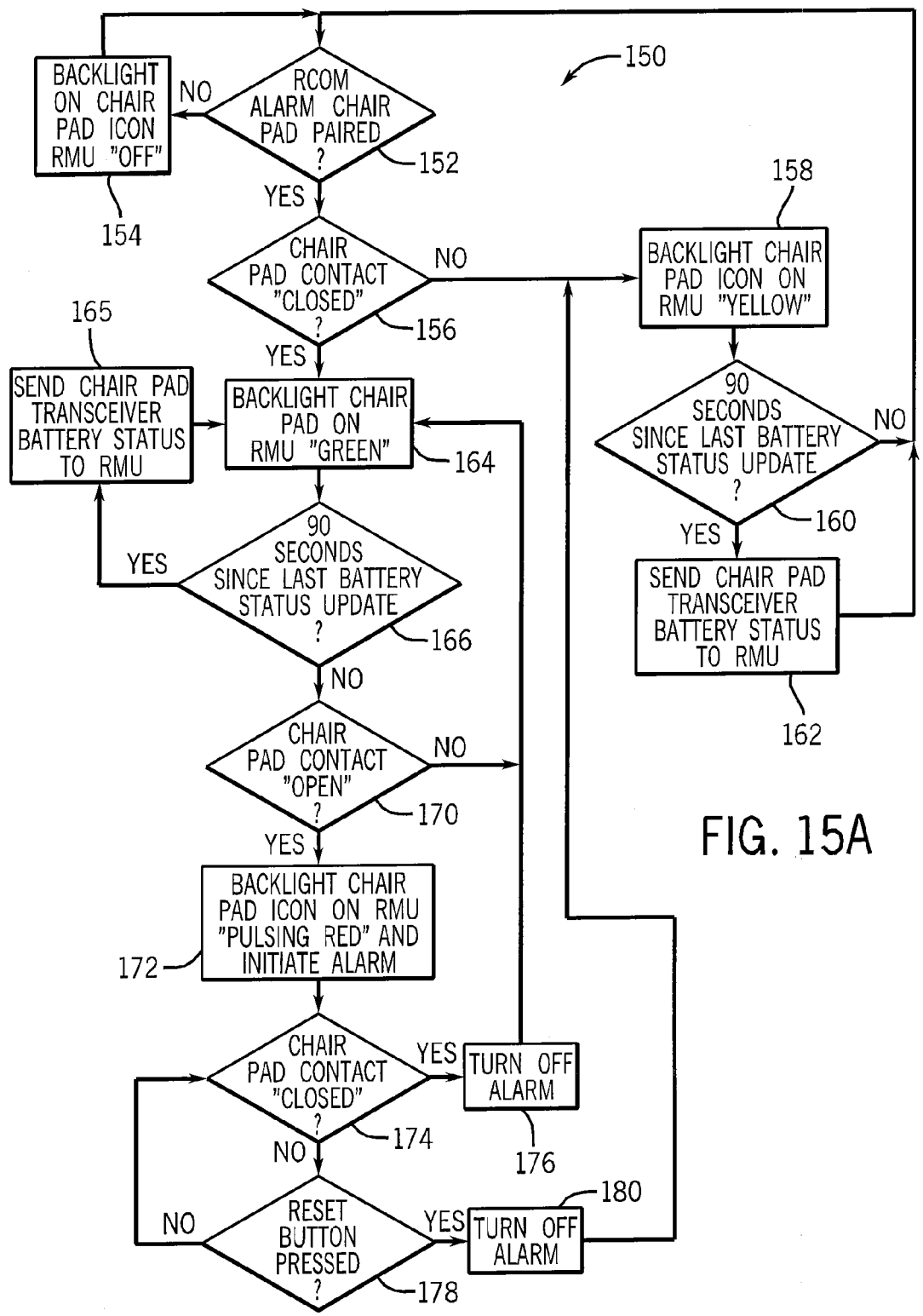
FIG. 15a is a flowchart executed by the room unit for controlling the chair alarm icon on the room unit display.

Referring now to FIG. 15A, a flowchart 150 illustrates a computer-implemented method for monitoring a state sensor unit, according to an exemplary embodiment using a chair sensor as an example. The method of flowchart 150 may be implemented using a room unit 34 and/or central monitoring unit 28. In a step 152, a determination is made whether a room unit is currently paired with a room sensor. If not, in a step 154, a backlight for chair unit icon 44c for the room unit 34 remains off. If yes, in a step 156, a determination is made whether the chair pad contact for the sensor is in a "CLOSED" position, indicative that the patient is seated in the chair. If no, the backlight for chair unit icon 44c for the room unit 34 is turned to "YELLOW" in a step 158 and a determination is made in a step 160 whether 90 seconds has elapsed since the last battery status update. If yes, a chair battery status update is transmitted to room unit 34 in a step 162.

If the chair pad contact for the sensor is in a "CLOSED" position in step 156, the backlight for chair unit icon 44c for the room unit 34 is turned to "GREEN" in a step 164, and a determination is made in a step 166 whether 90 seconds has elapsed since the last battery status update. If yes, a chair battery status update is transmitted to room unit 34 in a step 168. If no, the sensor is monitored for a change of state in a step 170. When the state changes, the backlight for chair unit icon 44c for the room unit 34 is turned to "PULSING RED" and an alarm condition is initiated in a step 172 until either the state is change back to "CLOSED" position in a step 174 and the alarm is turned off in a step 176 or the reset button 50 is pressed in a step 178 and the alarm is turned off in a step 180.

Figure 15B:
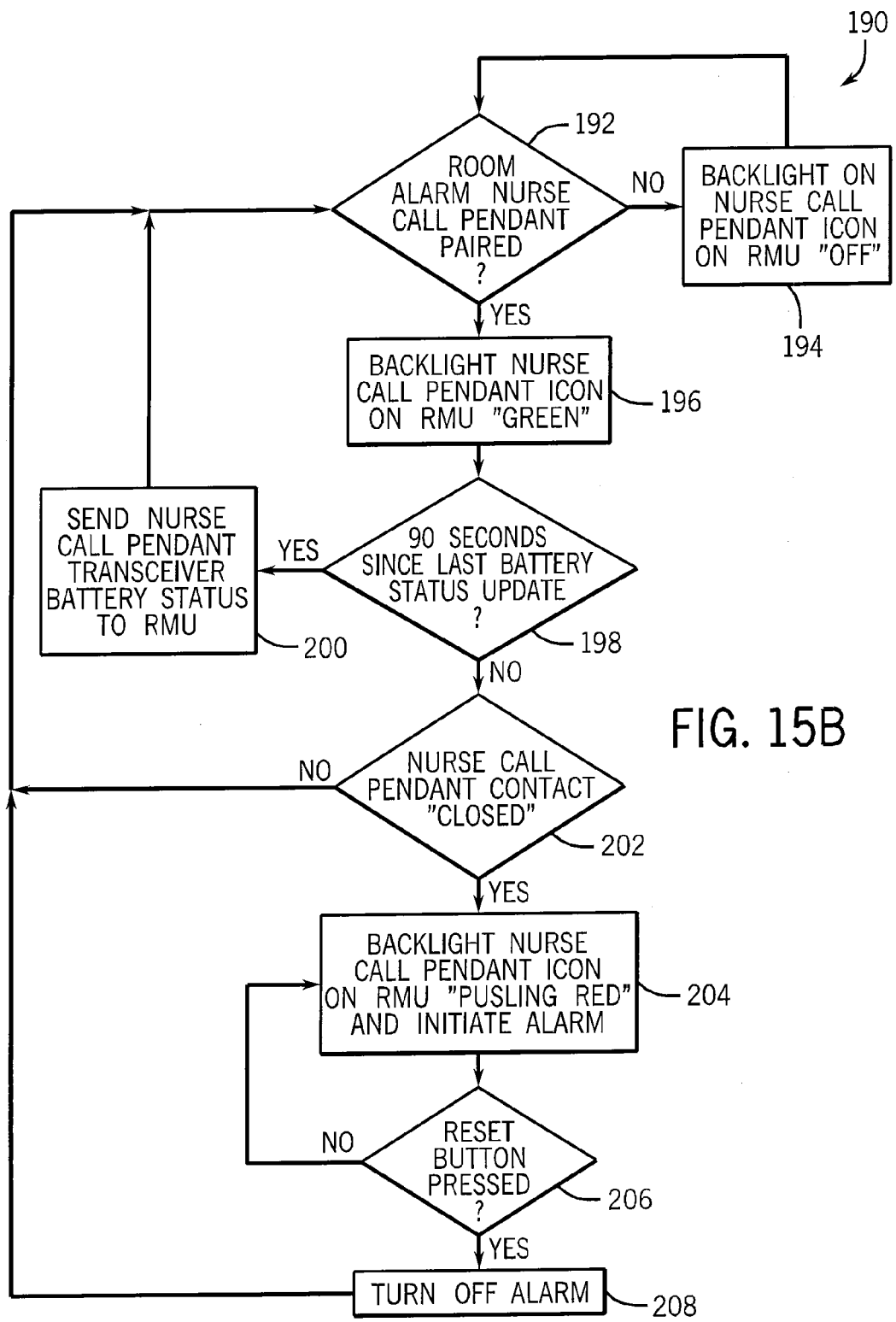
FIG. 15b is a flowchart executed by the room unit for controlling the nurse call icon on the room unit display.

Referring now to FIG. 15B, a flowchart 190 illustrates a computer-implemented method for monitoring a sensor unit according to an exemplary embodiment. The method of flowchart 190 may be implemented using a room unit 34 and/or central monitoring unit 28. In a step 192, a determination is made whether a room unit is currently paired with a room sensor, such as a nurse call button as described in this embodiment. If not, in a step 194, a backlight for nurse call icon 44a for the room unit 34 remains off. If yes, the backlight for nurse call icon 44a for the room unit 34 is turned to "GREEN" in a step 196 and a determination is made in a step 198 whether 90 seconds has elapsed since the last battery status update. If yes, a nurse call battery status update is transmitted to room unit 34 in a step 200. If not, a determination is made in a step 202 whether the nurse call contact for the sensor is in a "CLOSED" position, indicative that the button has been depressed. If yes, the backlight for nurse call icon 44a for the room unit 34 is turned to "PULSING RED" and an alarm condition is initiated in a step 204 until the reset button 50 is pressed in a step 206 and the alarm is turned off in a step 208.

It is specifically intended that the present invention not be limited to the embodiments and illustrations contained herein, but include modified forms of those embodiments including portions of the embodiments and combinations of elements of different embodiments as come within the scope of the following claims.

We claim:

1. A wireless patient monitoring system comprising:
   multiple sensor units each providing an input triggerable by a patient and transmitting a first radio signal including sensor identification data uniquely identifying the sensor unit and state data indicating a triggering of the input; and
   at least one room unit receiving the first radio signals of the sensor units, the room unit including a connection table mapping identification data to the room unit, the room unit selectively responding to first radio signals of sensor units mapped to the room unit by the connection table,
   wherein the room unit triggers a proximity sensor of a sensor unit when the sensor unit is at a distant less than the distance at which the room unit may detect the first radio signal from the sensor unit and wherein the connection table is populated by a detection of the identification data of the sensor in the first radio signal when the sensor unit proximity sensor is triggered by the proximity of the room unit.

2. The wireless patient monitoring system of claim 1 wherein the first radio signal further includes function data identifying a meaning of the triggering of the sensor unit.

3. The wireless patient monitoring system of claim 2 wherein the function data indicates a function selected from the group consisting of: indication of a state of a bed pressure pad, indication of a state of a chair pressure pad, indication of a state of a floor pressure pad, indication of a state of a patient call button.

4. The wireless patient monitoring system of claim 1 wherein the display is selected from a room name, a patient name, and graphic data indicating a room location.

5. The wireless patient monitoring system of claim 1 wherein the room unit provides at least one of an audio alarm and a display indicating a triggering of an input of sensor units mapped to the room unit.

6. The wireless patient monitoring system of claim 5 wherein the first radio signals further include function data identifying a function of the sensor units and wherein at least one audio alarm and a display indicates function data of sensor units whose state data indicates a triggering of an input of the sensor units.

7. The wireless patient monitoring system of claim 5 wherein the display indicates a triggering of an input of a sensor unit through a selected light color and light flashing pattern.

8. The wireless patient monitoring system ,of claim 1 wherein the sensor units include a battery power supply and the room unit includes a line voltage power supply with battery backup.

9. The wireless patient monitoring system of claim 8 wherein the first radio signal further includes battery data indicating battery strength.

10. The wireless patient monitoring system of claim 1 wherein the room unit further includes a reset button causing a transmission of the second radio signal indicating a caregiver response to the triggering of a sensor unit.

11. The wireless patient monitoring system of claim 1 wherein the connection table is depopulated by detection of an identification data of the sensor when the proximity sensor of the sensor unit is triggered by the close proximity of the room unit, and the sensor unit is already enrolled in the connection table.

12. The wireless patient monitoring system of claim 1 including a close-proximity sensor detecting a proximity of the room unit and a central unit,
   wherein the room unit is configured to transmit a second radio signal identifying the room unit when the central unit proximity is detected by the close proximity sensor,
   wherein the central unit is configured to maintain a room table based upon the second radio signal and the room table is populated at least in part by a detection of the room unit identification data of the room in the second radio signal
   wherein the second signal is configured to include state data from the first radio signals appended to room unit identification data.

13. The wireless patient monitoring system of claim 1 wherein the control the unit includes a user input device for entry of the morn identifier by a user.

14. The wireless patient monitoring, system of claim 1 further including one or more paging devices wherein the room unit is configured to receive and transmit information targeted to a paging device to both other room units and the paging device.

15. The wireless patient monitoring system of claim 14 wherein the sensor units include a battery power supply and the room unit includes a line voltage power supply.

16. The wireless patient monitoring system of claim 14 wherein the room unit further includes a reset button causing the ceasing of at least one of an audio alarm and visual display indicating a triggering of a sensor unit.

17. The wireless patient monitoring system of claim 14 further including one or more paging devices, wherein the room unit is configured to receive and transmit a second radio signal including state data from the first radio signals to a paging device.

18. A wireless patient monitoring system comprising:
   multiple battery powered sensor units each providing an input triggerable by a patient and transmitting a first radio signal including: identification data uniquely identifying the sensor unit, function data identifying a function implemented by the sensor unit, and battery state data indicating a state of a battery of the sensor unit; and state data indicating of a triggering of the input;
   at least one room unit receiving the first radio signals of the sensor units, the room unit including a connection table mapping identification data of given sensor units to the room unit, the room unit selectively responding to first radio signals only of given sensor units mapped to the room unit by the connection table to provide a visual indication indicating the triggering of the given sensor units, the function of the given sensor units that are triggered, the state of the battery of at least one of the given sensor units, and responding to an absence of first radio signals of at least one given sensor unit to indicate a loss of wireless connection,
   wherein the sensor units include a close-proximity sensor detecting proximity of the sensor unit and a room unit wherein the connection table is populated by a detection of the identification data of the sensor in the first radio signal when the room unit proximity is detected by the close proximity sensor.

19. A wireless patient monitoring system comprising:
   multiple sensor units each providing an input triggerable by a patient and transmitting a first radio signal including identification data uniquely identifying the sensor unit and state data indicating a triggering of the input; and at least one room unit receiving the first radio signals of the sensor units, the room unit including a connection table mapping identification data to the room unit, the room unit selectively responding to first radio signals of sensor units mapped to the room unit by the connection table to transmit a second radio signal including state data from the first radio signals and to provide at least one of an audio alarm and visual display of that state change, wherein the at least one room unit triggers a proximity sensor of a sensor unit when the sensor unit is at a distance less than the distance at which the at least one room unit may detect the first radio signal from at least one sensor unit and wherein the connection table is populated by a detection of the identification data of the sensor in the first radio signal when the at least one sensor unit proximity sensor is triggered by the proximity of the at least one room unit.

* * * * *